US011045579B2

(12) United States Patent
Barere et al.

(10) Patent No.: US 11,045,579 B2
(45) Date of Patent: Jun. 29, 2021

(54) BREAST TREATMENT DEVICE

(71) Applicant: LifeCell Corporation, Branchburg, NJ (US)

(72) Inventors: Aaron Barere, Hoboken, NJ (US); Sangwook Park, Dunellen, NJ (US); Kai-Roy Wang, Jersey City, NJ (US)

(73) Assignee: LifeCell Corporation, Madison, NJ (US)

( * ) Notice: Subject to any disclaimer, the term of this patent is extended or adjusted under 35 U.S.C. 154(b) by 0 days.

(21) Appl. No.: 15/691,865

(22) Filed: Aug. 31, 2017

(65) Prior Publication Data

US 2018/0055624 A1    Mar. 1, 2018

Related U.S. Application Data

(60) Provisional application No. 62/381,865, filed on Aug. 31, 2016.

(51) Int. Cl.
*A61F 2/12* (2006.01)
*A61L 27/36* (2006.01)
*A61L 27/56* (2006.01)
*A61F 2/00* (2006.01)

(52) U.S. Cl.
CPC ............. *A61L 27/362* (2013.01); *A61F 2/12* (2013.01); *A61L 27/3641* (2013.01); *A61L 27/3666* (2013.01); *A61L 27/3695* (2013.01); *A61L 27/56* (2013.01); *A61F 2/0063* (2013.01); *A61F 2210/0057* (2013.01); *A61F 2220/0008* (2013.01); *A61F 2230/0008* (2013.01); *A61F 2230/0013* (2013.01); *A61L 2430/04* (2013.01)

(58) Field of Classification Search
CPC ..................................... A61F 2/12; A61F 2/52
See application file for complete search history.

(56) References Cited

U.S. PATENT DOCUMENTS

| 2,108,205 A | 2/1938 | Martin |
| 3,683,424 A | 8/1972 | Pangman |
| 4,298,998 A | 11/1981 | Naficy |
| 4,840,629 A | 6/1989 | Bustos |
| 4,936,858 A | 6/1990 | O'Keeffe |
| 4,984,585 A | 1/1991 | Austad |
| 5,352,307 A | 10/1994 | Wild |

(Continued)

FOREIGN PATENT DOCUMENTS

| CN | 1953657 A | 4/2007 |
| DE | 102006029605 A1 | 12/2007 |

(Continued)

OTHER PUBLICATIONS

Baxter, Intracapsular allogenic dermal grafts for breast implant-related problems. Plast Reconstr Surg. Nov. 2003;112(6):1692-6.

(Continued)

*Primary Examiner* — Seema Mathew
(74) *Attorney, Agent, or Firm* — McCarter & English, LLP

(57) ABSTRACT

The present disclosure provides devices and methods for treating breasts. The devices can include an acellular tissue matrix having a predefined shape that allows for complete or enhanced coverage of an anterior portion of a breast implant or tissue expander or to support an implant and/or surrounding tissues.

7 Claims, 15 Drawing Sheets

(56) References Cited

U.S. PATENT DOCUMENTS

| | | | |
|---|---|---|---|
| 5,356,429 A | 10/1994 | Seare | |
| 5,447,535 A | 9/1995 | Muller | |
| 5,584,884 A * | 12/1996 | Pignataro | A61F 2/12 606/151 |
| 5,658,328 A | 8/1997 | Johnson et al. | |
| 5,658,330 A | 8/1997 | Carlisle et al. | |
| 5,676,161 A | 10/1997 | Breiner | |
| 5,713,959 A | 2/1998 | Bartlett et al. | |
| 5,733,337 A | 3/1998 | Carr, Jr. et al. | |
| 5,755,791 A | 5/1998 | Whitson et al. | |
| 5,954,767 A | 9/1999 | Pajotin et al. | |
| 5,968,096 A | 10/1999 | Whitson et al. | |
| 5,997,575 A | 12/1999 | Whitson et al. | |
| 6,099,566 A | 8/2000 | Vonderharr et al. | |
| 6,203,570 B1 | 3/2001 | Baeke | |
| 6,210,439 B1 | 4/2001 | Firmin et al. | |
| 6,334,868 B1 | 1/2002 | Ham | |
| 6,368,541 B1 | 4/2002 | Pajotin et al. | |
| 6,638,308 B2 | 10/2003 | Corbitt, Jr. et al. | |
| 6,666,892 B2 | 12/2003 | Hiles et al. | |
| 6,723,133 B1 | 4/2004 | Pajotin | |
| 6,736,823 B2 | 5/2004 | Darois et al. | |
| 6,736,854 B2 | 5/2004 | Vadurro et al. | |
| 6,740,122 B1 | 5/2004 | Pajotin | |
| 6,777,231 B1 | 8/2004 | Katz et al. | |
| 6,802,861 B1 | 10/2004 | Hamas | |
| 7,011,688 B2 | 3/2006 | Gryska et al. | |
| 7,081,135 B2 | 7/2006 | Smith et al. | |
| 7,358,284 B2 | 4/2008 | Griffey et al. | |
| 7,470,537 B2 | 12/2008 | Hedrick et al. | |
| 7,476,249 B2 | 1/2009 | Frank | |
| 7,658,727 B1 | 2/2010 | Fernandes et al. | |
| 7,699,895 B2 | 4/2010 | Hiles et al. | |
| 7,875,074 B2 | 1/2011 | Chen et al. | |
| 8,007,531 B2 * | 8/2011 | Frank | A61F 2/12 623/8 |
| 8,128,708 B2 | 3/2012 | Hiles et al. | |
| 8,192,486 B2 | 6/2012 | Glicksman | |
| 8,313,527 B2 | 11/2012 | Powell et al. | |
| 8,383,092 B2 | 2/2013 | Lee et al. | |
| 8,487,012 B2 | 7/2013 | Goraltchouk et al. | |
| 8,685,296 B2 | 4/2014 | Liu et al. | |
| 8,858,647 B2 | 10/2014 | Markman | |
| 8,876,899 B2 | 11/2014 | Maxwell | |
| 8,986,377 B2 * | 3/2015 | Richter | A61F 2/12 623/8 |
| 9,433,489 B2 * | 9/2016 | Reilly | D04C 1/06 |
| 9,549,812 B2 | 1/2017 | Shetty et al. | |
| 9,681,941 B2 * | 6/2017 | Griffin | A61F 2/0063 |
| 9,913,711 B2 * | 3/2018 | Rehnke | A61F 2/12 |
| 9,956,072 B2 * | 5/2018 | Diaz | A61B 90/02 |
| 10,004,590 B2 | 6/2018 | Shetty et al. | |
| 10,258,460 B2 * | 4/2019 | Moses | A61B 18/00 |
| 10,398,542 B2 * | 9/2019 | Griffin | A61B 17/06166 |
| 10,405,969 B2 | 9/2019 | Bertoli et al. | |
| 10,433,947 B2 * | 10/2019 | Khouri | A61H 7/00 |
| 10,449,034 B2 | 10/2019 | Bowley et al. | |
| 10,660,741 B2 * | 5/2020 | Doucet | A61F 2/12 |
| 10,842,612 B2 * | 11/2020 | Barere | A61L 27/3633 |
| 2001/0041936 A1 | 11/2001 | Corbitt et al. | |
| 2002/0103542 A1 | 8/2002 | Bilbo | |
| 2003/0036803 A1 | 2/2003 | McGhan | |
| 2003/0130747 A1 | 7/2003 | Abraham et al. | |
| 2003/0212461 A1 | 11/2003 | Vadurro et al. | |
| 2003/0212462 A1 | 11/2003 | Gryska et al. | |
| 2003/0225355 A1 | 12/2003 | Butler | |
| 2004/0049269 A1 | 3/2004 | Corbitt et al. | |
| 2004/0260315 A1 | 12/2004 | Dell et al. | |
| 2005/0021141 A1 | 1/2005 | Bleyer et al. | |
| 2005/0119737 A1 | 6/2005 | Bene et al. | |
| 2005/0165425 A1 | 7/2005 | Croce et al. | |
| 2005/0187624 A1 | 8/2005 | Corbitt | |
| 2005/0250977 A1 | 11/2005 | Montpetit et al. | |
| 2005/0260176 A1 | 11/2005 | Ayares et al. | |
| 2006/0030939 A1 | 2/2006 | Frank | |
| 2006/0167338 A1 | 7/2006 | Shfaram | |
| 2006/0206189 A1 | 9/2006 | Furst et al. | |
| 2007/0038299 A1 | 2/2007 | Stone et al. | |
| 2007/0088299 A1 | 4/2007 | Ayre | |
| 2007/0088434 A1 | 4/2007 | Frank | |
| 2007/0116678 A1 | 5/2007 | Sung et al. | |
| 2007/0250177 A1 | 10/2007 | Bilbo | |
| 2008/0027273 A1 | 1/2008 | Gutterman | |
| 2008/0027542 A1 | 1/2008 | McQuillan et al. | |
| 2008/0082113 A1 | 4/2008 | Bishop et al. | |
| 2008/0097601 A1 | 4/2008 | Codori-Hurff et al. | |
| 2008/0108134 A1 | 5/2008 | Murphy et al. | |
| 2008/0167729 A1 | 7/2008 | Nelson et al. | |
| 2008/0241212 A1 | 10/2008 | Moses et al. | |
| 2008/0260853 A1 | 10/2008 | Firestone | |
| 2008/0281418 A1 | 11/2008 | Firestone | |
| 2008/0281419 A1 | 11/2008 | Matheny et al. | |
| 2009/0024227 A1 | 1/2009 | Lesh | |
| 2009/0024228 A1 | 1/2009 | Lesh | |
| 2009/0082864 A1 | 3/2009 | Chen et al. | |
| 2009/0125107 A1 | 5/2009 | Maxwell | |
| 2009/0198332 A1 | 8/2009 | Becker | |
| 2009/0216338 A1 | 8/2009 | Gingras et al. | |
| 2009/0240342 A1 | 9/2009 | Lindh, Sr. et al. | |
| 2010/0010627 A1 | 1/2010 | Matheny | |
| 2010/0023029 A1 | 1/2010 | Young | |
| 2010/0028396 A1 | 2/2010 | Ward et al. | |
| 2010/0191330 A1 | 7/2010 | Lauryssen et al. | |
| 2010/0217388 A1 * | 8/2010 | Cohen | A61F 2/12 623/8 |
| 2010/0226960 A1 | 9/2010 | Chudzik et al. | |
| 2010/0303880 A1 | 12/2010 | Reddy et al. | |
| 2010/0303886 A1 | 12/2010 | Janis | |
| 2011/0009960 A1 | 1/2011 | Altman et al. | |
| 2011/0022171 A1 | 1/2011 | Richter et al. | |
| 2011/0035004 A1 | 2/2011 | Maxwell | |
| 2011/0082481 A1 | 4/2011 | Gingras et al. | |
| 2011/0151011 A1 | 6/2011 | Flynn | |
| 2011/0177150 A1 | 7/2011 | Pathak et al. | |
| 2011/0276039 A1 | 11/2011 | Markman | |
| 2011/0293666 A1 | 12/2011 | Wang et al. | |
| 2011/0293667 A1 | 12/2011 | Baksh et al. | |
| 2012/0052040 A1 | 3/2012 | Hunter et al. | |
| 2012/0158134 A1 | 6/2012 | Codori-Hurff et al. | |
| 2012/0255047 A1 | 10/2012 | Phelps et al. | |
| 2012/0283826 A1 | 11/2012 | Moses et al. | |
| 2013/0053956 A1 | 2/2013 | Powell et al. | |
| 2013/0085579 A1 | 4/2013 | Markman | |
| 2013/0224260 A1 | 8/2013 | Ward et al. | |
| 2013/0261745 A1 | 10/2013 | Van Epps | |
| 2013/0273145 A1 | 10/2013 | Vail | |
| 2014/0039617 A1 | 2/2014 | Maxwell | |
| 2014/0141053 A1 | 5/2014 | Guillemette et al. | |
| 2014/0257481 A1 | 9/2014 | Brooks et al. | |
| 2014/0257482 A1 | 9/2014 | Ward et al. | |
| 2014/0276993 A1 | 9/2014 | Reilly et al. | |
| 2015/0012089 A1 | 1/2015 | Shetty et al. | |
| 2015/0119353 A1 | 4/2015 | Vail | |
| 2015/0150674 A1 | 6/2015 | Ansorge et al. | |
| 2015/0157451 A1 * | 6/2015 | Bowley | A61F 2/12 623/8 |
| 2015/0223928 A1 * | 8/2015 | Limem | A61F 2/12 623/8 |
| 2015/0250582 A1 * | 9/2015 | Greenhalgh | A61L 31/14 623/8 |
| 2015/0313708 A1 | 11/2015 | Mayo Martin | |
| 2015/0359622 A1 | 12/2015 | Matheny | |
| 2015/0359933 A1 | 12/2015 | Matheny | |
| 2015/0374830 A1 | 12/2015 | McKay | |
| 2016/0108144 A1 | 4/2016 | Vail | |
| 2016/0199173 A1 | 7/2016 | Liu et al. | |
| 2016/0228236 A1 * | 8/2016 | Egnelov | A61F 2/12 |
| 2016/0256259 A1 * | 9/2016 | Wirth | A61L 27/3633 |
| 2016/0324618 A1 * | 11/2016 | Greenhalgh | A61L 31/14 |
| 2016/0331504 A1 | 11/2016 | Wang et al. | |
| 2017/0007394 A1 | 1/2017 | Shetty et al. | |
| 2017/0027678 A1 * | 2/2017 | Greenhalgh | A61L 31/005 |
| 2017/0056157 A1 | 3/2017 | Hayzlett | |
| 2017/0065822 A1 | 3/2017 | Mashiach et al. | |

(56) References Cited

U.S. PATENT DOCUMENTS

| | | | |
|---|---|---|---|
| 2017/0071725 A1* | 3/2017 | Barere | A61L 27/3633 |
| 2017/0100509 A1 | 4/2017 | Sun et al. | |
| 2017/0340437 A1 | 11/2017 | Bowley et al. | |
| 2017/0348088 A1* | 12/2017 | Bunce | A61F 2/105 |
| 2017/0367807 A1* | 12/2017 | Chen | A61L 27/3691 |
| 2018/0092737 A1* | 4/2018 | Barere | A61L 27/3604 |
| 2018/0228598 A1* | 8/2018 | Math Isen | A61L 27/56 |
| 2019/0201580 A1* | 7/2019 | Barere | A61F 2/12 |
| 2020/0008930 A1* | 1/2020 | Bowley | A61L 27/3695 |
| 2020/0078165 A1* | 3/2020 | Spiegel | A61F 2/0063 |
| 2020/0107921 A1* | 4/2020 | Mathisen | A61F 2/12 |
| 2020/0222177 A1* | 7/2020 | Paydar | A61F 2/12 |
| 2020/0230292 A1* | 7/2020 | Park | A61L 27/3645 |
| 2020/0246506 A1* | 8/2020 | Xu | A61L 27/3633 |
| 2020/0268498 A1* | 8/2020 | Reddy | A61F 2/0063 |

FOREIGN PATENT DOCUMENTS

| | | |
|---|---|---|
| FR | 2682284 A1 | 4/1993 |
| FR | 2746298 A1 | 9/1997 |
| JP | H09-47503 A | 2/1997 |
| JP | H10-158906 | 6/1998 |
| JP | 2005-536228 A | 12/2005 |
| RU | 2288674 C2 | 12/2006 |
| WO | WO-2004/096098 A1 | 11/2004 |
| WO | 2005/089411 A2 | 9/2005 |
| WO | 2006/115892 A2 | 11/2006 |
| WO | WO-2006/135998 A2 | 12/2006 |
| WO | 2007/004214 A2 | 1/2007 |
| WO | 2007/134134 A2 | 11/2007 |
| WO | 2008/016919 A2 | 2/2008 |
| WO | 2008/121816 A2 | 10/2008 |
| WO | 2009/001293 A1 | 12/2008 |
| WO | 2009/065013 A1 | 5/2009 |

OTHER PUBLICATIONS

Bindingnavele et al., Use of acellular cadaveric dermis and tissue expansion in postmastectomy breast reconstruction. J Plast Reconstr Aesthet Surg. 2007;60(11):1214-8.

Breuing et al., Immediate bilateral breast reconstruction with implants and inferolateral AlloDerm slings. Ann Plast Surg. Sep. 2005;55(3):232-9.

Breuing et al., Inferolateral AlloDerm hammock for implant coverage in breast reconstruction. Ann Plast Surg. Sep. 2007;59(3):250-5.

Colwell et al., Improving shape and symmetry in mastopexy with autologous or cadaveric dermal slings. Ann Plast Surg. Aug. 2008;61(2):138-42.

Darcy, A technique for preparing meshed skin grafts with planned expansion ratios. Br J Plast Surg. Jan. 2003;56(1):77-9.

Duncan, Correction of implant rippling using allograft dermis. Aesthet Surg J. Jan. 2001;21(1):81-4.

Gamboa-Bobadilla, Implant breast reconstruction using acellular dermal matrix. Ann Plast Surg. Jan. 2006;56(1):22-5.

Góes et al., The application of mesh support in periareolar breast surgery: clinical and mammographic evaluation. Aesthetic Plast Surg. Sep.-Oct. 2004;28(5):268-74.

Góes, Periareolar mammaplasty: double skin technique with application of polyglactine or mixed mesh. Plast Reconstr Surg. Apr. 1996;97(5):959-68.

Góes, Periareolar Mammaplasty: Double Skin Technique with Appliction of Polygractine 910 Mesh. Rev. Soc. Bras. Cir. Plast. Estet. Reconstr. Jan./Dec. 1992;7(1,2,3):1-5.

Góes, Periareolar Mastopexy and Reduction with Mesh Support, Double Skin Technique. Surgery of the Breast: Principles and Art. Scott L. Spear (Ed.), Lippincott-Raven Publishers, Philadelphia. Chapter 51, pp. 697-708 (1998).

Góes, Periareolar Mastopexy: Double Skin Techique with Mess Support. Aesthetic Surgery Journal. Mar.-Apr. 2003;23:129-135.

Góes, Periareolar Mammaplasty with Mixed Mesh Support: The Double Skin Technique. Operative Techniques in Plastic and Reconstructive Surgery. Aug. 1996;3(3):199-206.

MTF—Musculoskeletal Transplant Foundation, FlexHD® Pliable™ Acellular Dermis, donated human tissue. Instructions, 2 pages. Mar. 2012.

MTF—Musculoskeletal Transplant Foundation, FlexHD® Structural, The Better Approach to a Better Allograft. 6 pages, (2012).

MTF—Musculoskeletal Transplant Foundation, FlexHD® Pliable Max, Designed by Surgeons to Build a Better Breast™. 4 pages, (2016).

Pope, Mesh Skin Grafting. Veterinary Clinics of North America: Small Animal Practice. Jan. 1990;20(1):177-187.

Salzberg, Nonexpansive immediate breast reconstruction using human acellular tissue matrix graft (AlloDerm). Ann Plast Surg. Jul. 2006;57(1):1-5.

Topol et al., Immediate single-stage breast reconstruction using implants and human acellular dermal tissue matrix with adjustment of the lower pole of the breast to reduce unwanted lift. Ann Plast Surg. Nov. 2008;61(5):494-9.

Zienowicz et al., Implant-based breast reconstruction with allograft. Plast Reconstr Surg. Aug. 2007;120(2):373-81.

International Search Report for Application No. PCT/US2017/049516, dated Dec. 15, 2017. 7 pages.

* cited by examiner

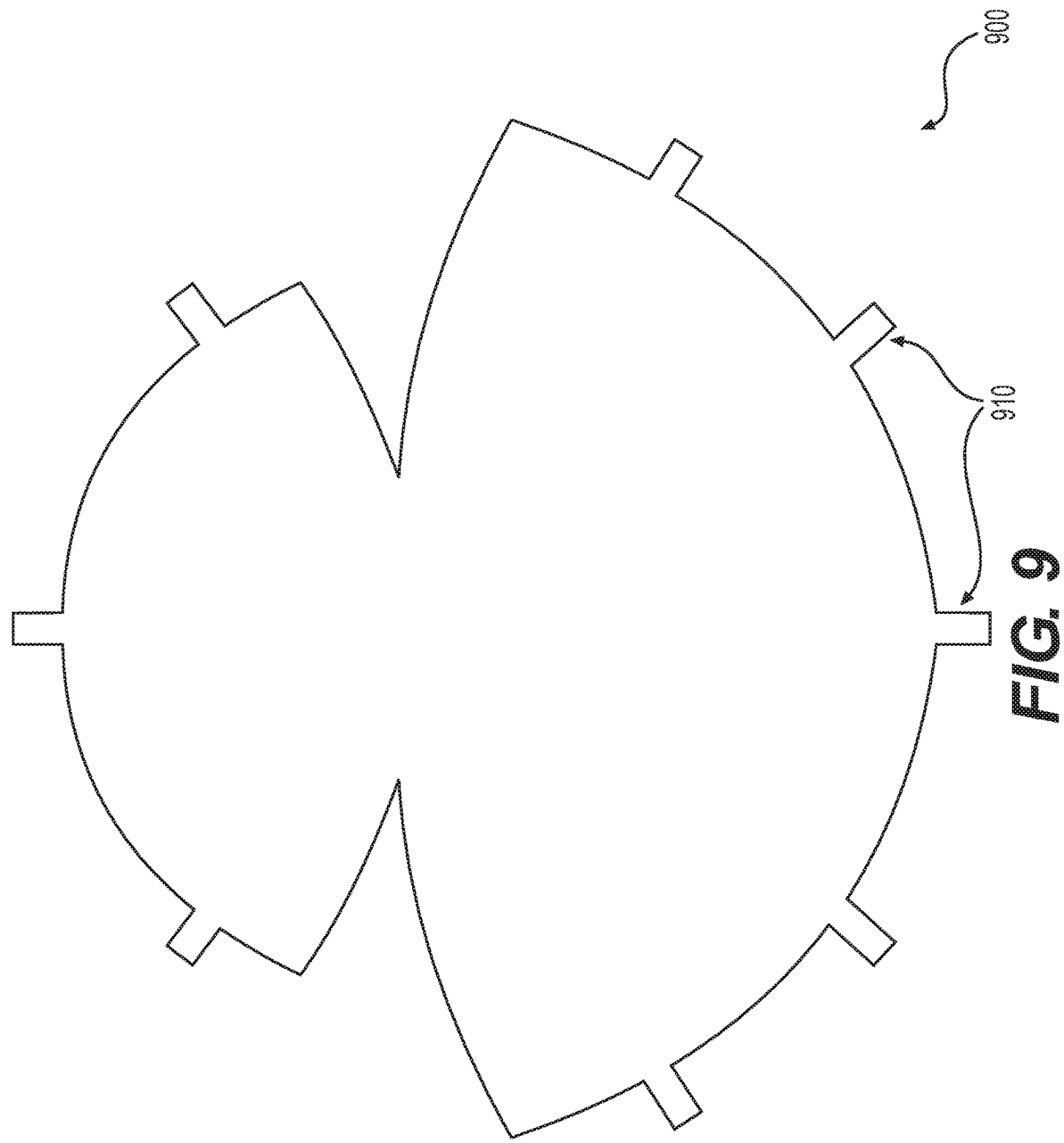

BREAST TREATMENT DEVICE

This application claims priority under 35 USC § 119 to U.S. Provisional Application No. 62/381,865, which was filed on Aug. 31, 2016 and is hereby incorporated by reference in its entirety.

The present disclosure relates generally to devices for improving breast surgeries, including tissue matrices specially shaped and sized for breast reconstruction or augmentation.

The use of acellular tissue matrices such as ALLODERM®, a dermal acellular matrix produced by LIFECELL® CORPORATION (Branchburg, N.J.), for use in breast procedures has become increasingly popular with plastic surgeons. Such materials provide a number of advantages and can be used to replace or augment supportive structures after, for example, mastectomy. Such materials can also be useful in reconstructive or aesthetic procedures (e.g., breast augmentation) by providing additional support for breast implants, allowing improved control of breast shape, preventing skin rippling, and/or preventing or treating other problems that may occur with breast augmentation (e.g., symmastia and bottoming out.)

For many surgical procedures, in order to achieve desired results, surgeons must alter the shape of sheets of tissue matrices. However, correctly forming the necessary shapes and implanting the materials properly can be time consuming, especially for less experienced surgeons. Furthermore, tissue matrices such as acellular dermal matrices can be expensive. Accordingly, requiring surgeons to reshape or resize relatively large pieces of such materials is not cost effective. To improve both surgical results and efficiency (in terms of both operative time and cost), pre-sized or pre-shaped tissue matrices can be beneficial. In addition, to provide coverage to select portions of implants or tissue matrices (e.g., the anterior surface or skin-contacting surface) improved, pre-formed shapes may be useful. Furthermore, matrices that are sized and shaped to facilitate complete coverage of the implant, complete coverage of selected parts (the anterior portion and/or parts of the superior/inferior/lateral/posterior implant), and/or attachment to surrounding structures can be useful. In addition, matrices sized and shaped to provide support to the breast and/or an implant, or to reinforce, augment, or otherwise protect or improve the quality of the overlying dermal tissue in prepectoral or other breast reconstructive procedures is desired for some patients.

The present application provides improved breast treatment devices including tissue matrix materials specially shaped and/or sized to improve surgical breast procedures.

Accordingly, in some embodiments, a breast treatment device is provided. The device can include a sheet of acellular tissue matrix, wherein the sheet of acellular tissue matrix comprises a flexible sheet with a top surface and a bottom surface, wherein the sheet has a first section and a second section, and the first and second sections have different shapes and are attached to one another, and wherein the first section includes curved first and second edges, and the second section includes curved first and second edges.

In some embodiments, a breast treatment device is provided. The device can include a sheet of acellular tissue matrix, wherein the sheet of acellular tissue matrix comprises a flexible sheet with a top surface and a bottom surface, wherein the sheet has an upper curved border having a first degree of curvature and a lower curved border having a second degree of curvature, wherein the lower curved border is shaped and sized to conform to a desired shape of a lower margin of a breast, and wherein the upper curved border is sized and shaped such that the flexible sheet of acellular tissue matrix can cover substantially all of the anterior surface of a breast implant or tissue expander when implanted in a breast.

In some embodiments, a breast treatment device is provided. The device can include a sheet of acellular tissue matrix, wherein the sheet of acellular tissue matrix comprises a flexible sheet with a top surface and a bottom surface, wherein the sheet comprises a lower curved border and an upper curved border, wherein the upper curved border and lower curved border are joined at apices at lateral ends of the device, and the sheet is symmetrically shaped about an axis midway between the apices and parallel to the top and bottom surfaces when lying on a flat surface, wherein the lower border forms a single outward arc shape, and wherein the upper border has three arc sections including first and second sections each extending from one of the apices, and a third section joining the first and second sections, the third section having a degree of curvature that is different than the degree of curvature of the first and section sections.

In some embodiments, a breast treatment device is provided. The device can include a sheet of acellular tissue matrix, wherein the sheet of acellular tissue matrix comprises a flexible sheet with a top surface and a bottom surface, wherein the sheet has an upper curved border having a first degree of curvature and a lower curved border having a second degree of curvature, wherein the lower curved border is shaped and sized to conform to a desired shape of a lower margin of a breast, and wherein the sheet is sized and shaped to provide an interface between subcutaneous tissue and the entire anterior surface of a breast implant or tissue expander.

Also provided are methods of treatment that include implanting the disclosed devices within a breast along with a breast implant or tissue expander.

BRIEF DESCRIPTION OF THE DRAWINGS

Reference will now be made to exemplary embodiments, examples of which are illustrated in the accompanying drawings. Wherever possible, the same reference numbers will be used throughout the drawings to refer to the same or like parts. The drawings are not necessarily to scale.

FIG. 9 illustrates a breast treatment device for more complete coverage of a breast implant or tissue expander and/or support or reinforcement of surrounding tissues, wherein the device further includes preformed tabs or extensions for attachment to tissue, according to certain embodiments.

DESCRIPTION OF EXEMPLARY EMBODIMENTS

Figure 1:
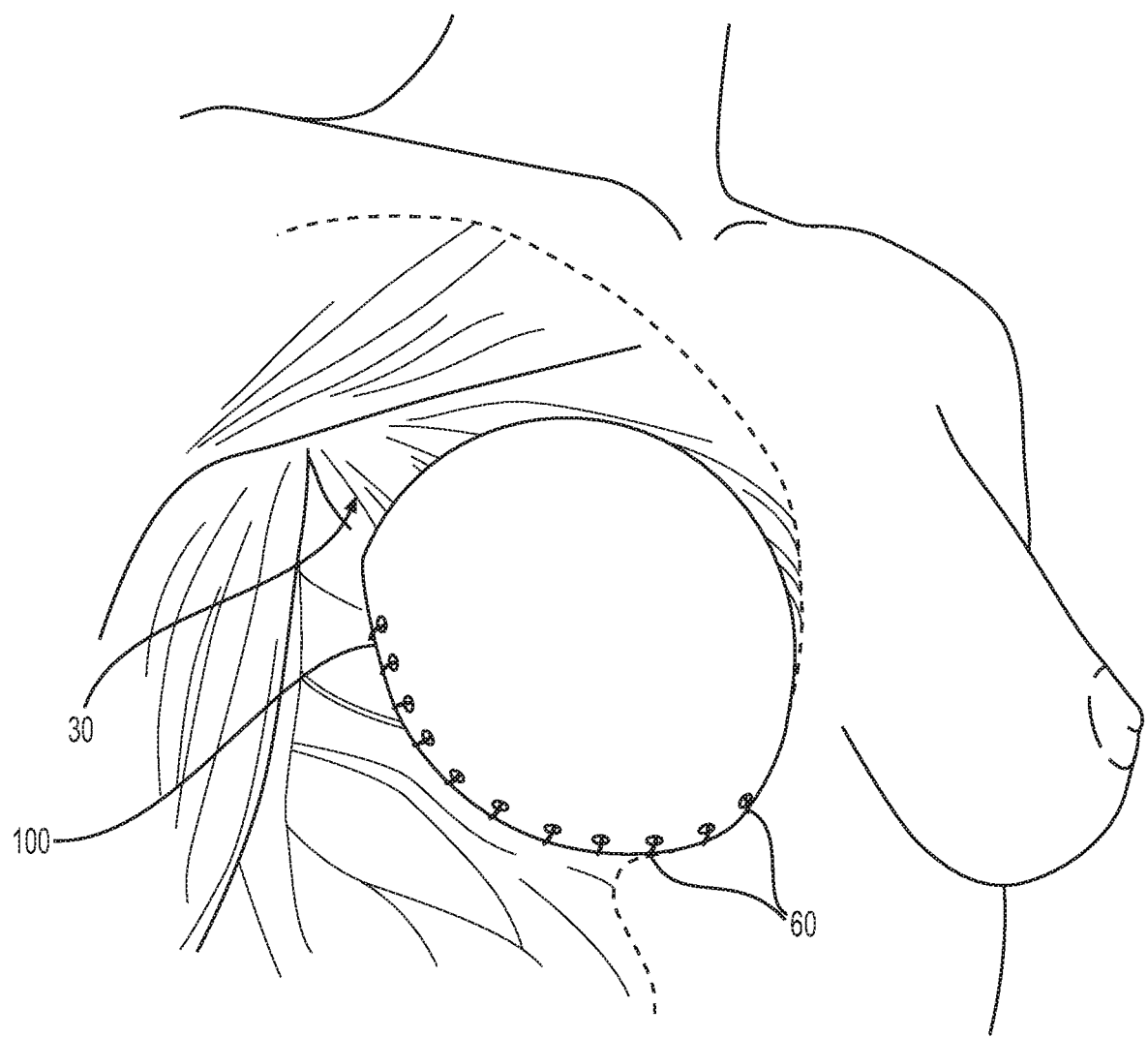
FIG. 1 illustrates a breast treatment device for more complete coverage of a breast implant or tissue expander in a pre-pectoral position, according to certain embodiments.

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The present disclosure relates generally to devices for surgical breast procedures and systems and methods relating to such devices. The devices can be used for tissue augmentation, repair or regeneration of damaged tissue, and/or correction of tissue defects. As such, the devices, systems, and methods discussed herein can be suitable for a wide range of surgical applications, such as, for example, aesthetic surgery, breast reconstruction, breast augmentation, breast enhancement, breast reduction, and revisionary breast surgeries.

The tissue matrices used to produce the devices described herein can include a variety of different materials. For example, an acellular tissue matrix or other tissue product can be selected to allow tissue ingrowth and remodeling to assist in regeneration of tissue normally found at the site where the matrix is implanted. For example, an acellular tissue matrix, when implanted on or into subdermal tissue, fascia, mammary tissue, muscle, bone, adipose or other tissue, may be selected to allow regeneration of the tissue without excessive fibrosis or scar formation. In certain embodiments, the devices can be formed from ALLODERM® or STRATTICE™ (LIFECELL® CORPORATION, BRANCHBURG, N.J.) which are human and porcine acellular dermal matrices, respectively. Alternatively, other suitable acellular tissue matrices can be used. For example, a number of suitable biological scaffold materials are described by Badylak et al. "Extracellular Matrix as a Biological Scaffold Material: Structure and Function," *Acta Biomaterialia* (2008), doi:10.1016/j.actbio.2008.09.013. The devices described herein can be produced from a variety of different human or animal tissues including human, porcine, ovine, bovine, or other animals tissues.

Tissue matrix products, such as acellular dermal tissue matrices, are widely used in surgical breast procedures. For example, sheets of acellular dermal matrix can be provided as a square or rectangular sample, which can be cut to a desired shape if needed. In addition, certain preformed tissue matrix shapes are available. For example, crescent or other curved shapes are available to reduce the amount of tissue matrix needed while providing an appropriate shape for an aesthetically desirable surgical result.

For some surgical applications, however, different shapes and sizes for tissue matrices would be beneficial. For example, when implanting a breast implant or tissue expander in a pre-pectoral position, i.e., anterior to the pectoral muscles, it would be beneficial in some cases to provide a tissue matrix shape and size that allows one or more of (1) complete or near complete anterior coverage of an implant or tissue expander, (2) minimized need for resizing or shaping the tissue matrix, or (3) preshaped borders that facilitate attachment to anatomical structures to produce desired surgical results (e.g., aesthetic or reconstructive result with low likelihood of complications).

FIG. 1 illustrates a breast treatment device 100 for more complete coverage of a breast implant or tissue expander in a pre-pectoral position and/or to support a breast implant or tissue expander, or help regenerate, reinforce, augment, or support surrounding tissue such as overlying dermis and subdermal tissue, according to certain embodiments. Although the devices and methods discussed herein are made with respect to, primarily, prepectoral procedures, the devices can be used by surgeons for other procedures. The device 100 can include a flexible sheet of acellular tissue matrix, as discussed above. As discussed in more detail below, the device 100 can be affixed to a chest wall 30 or other appropriate tissue to cover an implant or tissue expander (not shown in FIG. 1). The device can be secured in place using sutures 60 or other surgical fixation devices (e.g., staples, clips, surgical adhesives).

Figure 2:
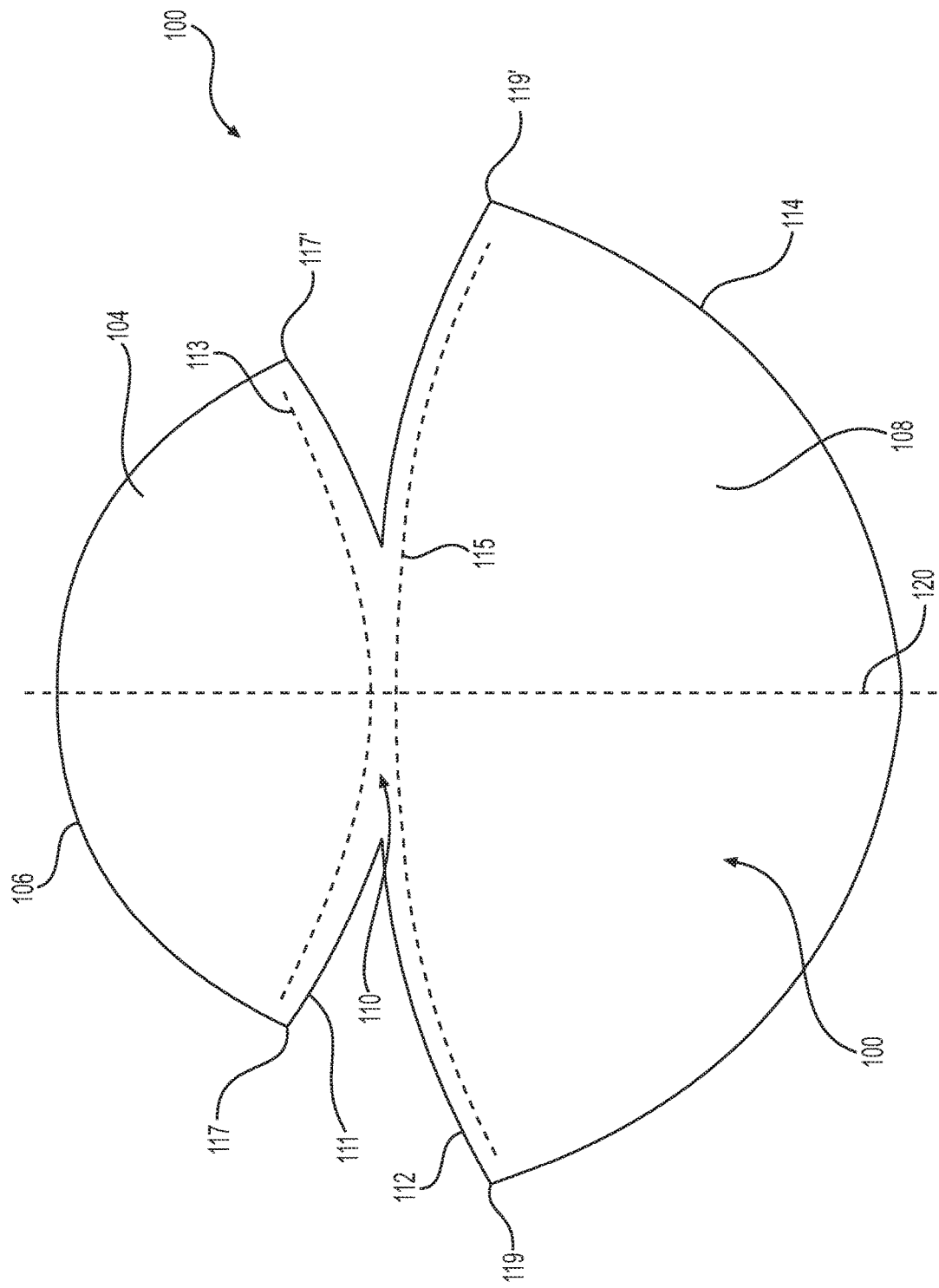
FIG. 2 illustrates a breast treatment device for more complete coverage of and/or support of a breast implant or tissue expander, according to certain embodiments.
Figure 3:
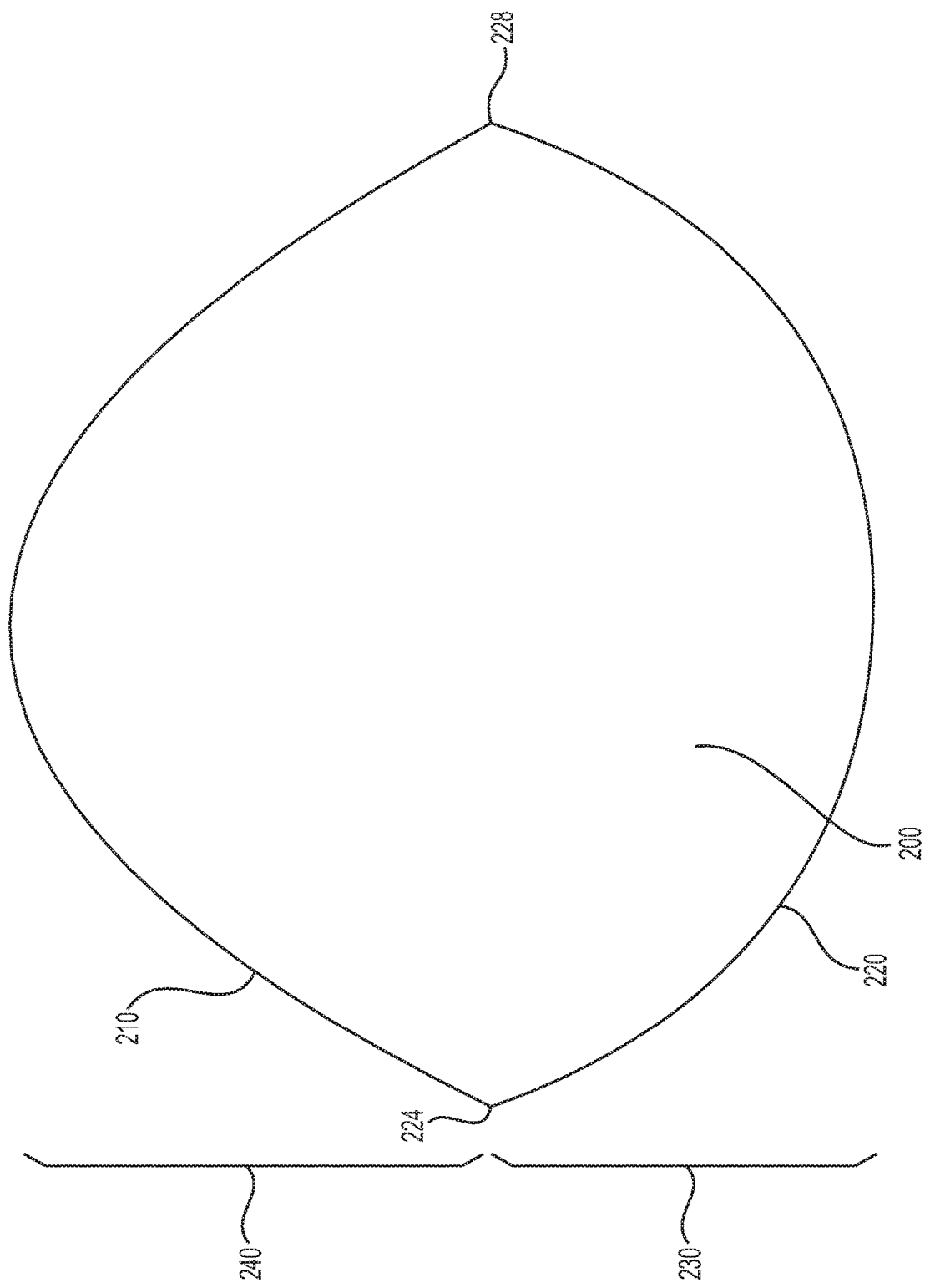
FIG. 3 illustrates another breast treatment device for more complete coverage of and/or support of a breast implant or tissue expander, according to certain embodiments.
Figure 4:
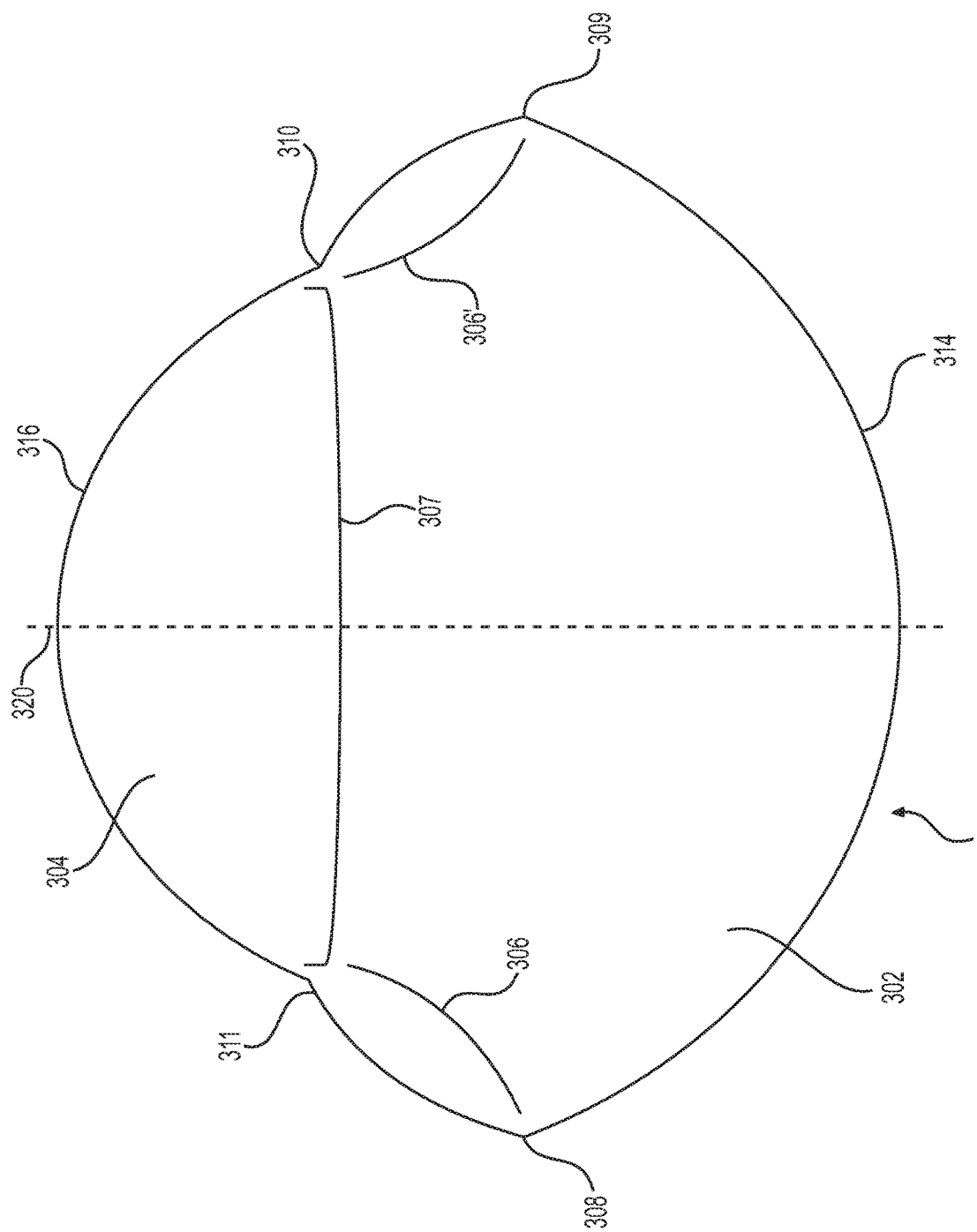
FIG. 4 illustrates another breast treatment device for more complete coverage of and/or support of a breast implant or tissue expander, according to certain embodiments.

FIGS. 2-4 are top views of various embodiments of devices, according to the present disclosure. The devices illustrated in FIGS. 2-4 can each include flexible sheets of acellular tissue matrix, which can have one of the illustrated shapes when laid flat. Each of the devices 100, 200, 300, can allow complete or substantially complete coverage of the anterior portion of a breast implant or tissue expander, including an implant or tissue expander positioned anterior to the pectoralis muscles. In addition, or alternatively, the devices can help support a breast implant or tissue expander, or help regenerate, reinforce, augment, or support surrounding tissue such as overlying dermis and subdermal tissue. When placed in contact with overlying tissue, the tissue matrix will support tissue regeneration, ultimately becoming infiltrated by cells and becoming vascularized, thereby providing enhanced tissue coverage to improve surgical outcomes, e.g., by preventing various possible adverse events such as rippling, loss of tissue integrity.

FIG. 2 illustrates a breast treatment device 100 for more complete coverage of a breast implant or tissue expander and/or to support a breast implant or tissue expander, or help regenerate, reinforce, augment, or support surrounding tissue such as overlying dermis and subdermal tissue, according to certain embodiments. As shown, the device 100 includes a sheet of acellular tissue matrix. The sheet can include a top surface and a bottom surface (the surfaces correspond to the front and back of the two-dimensional image of FIG. 2).

The sheet forming the device 100 has a first section 104 and a second section 108, and the first 104 and second 108 sections have different shapes and are attached to one another at a joining section 110. The first section includes curved first 106 and second edges 111, and the second section includes curved first 114 and second edges 112.

The curvature of the edges 106, 111, 114, 112 of the first 104 and second 108 sections can be varied to produce a desired shape. For example, in one embodiment the first edge 106 of the first section 104 has a degree of curvature that is greater than a degree of curvature of the second edge 111 of the first section 104. In addition, the first edge 114 of the second section 108 can have a degree of curvature that is greater than a degree of curvature of the second edge 112 of the second section 108. As shown, the first edges 106, 114 of the sections 104, 108 are the edges at opposite ends of the device 100.

The second edge 111 and second edge 112 will be understood to refer to a curved edge extending from opposite apices 117/117', 119/119' of the sections 104, 108 (i.e., edges along dashed lines 113, 115). But, as shown in FIG. 2, the sections 104 and 108 are joined at a joining section 110, such that the first section 104 and second section 108 are attached to one another along the second edges 111, 112 of each of the first section 104 and second section 108. The joining section 110 may simply be a continuation of a single sheet of acellular tissue matrix forming the device 100. As shown, the apices 117/117', 119/119' are pointed to form an acute angle, but the apices may alternatively be curved or rounded.

The device 100 is illustrated as having two-dimensional symmetry about a line or axis 120 passing midway through the tissue matrix 100 when the device lies flat. Variations in the shape may be made, or the device may be made nearly or perfectly symmetric. Furthermore, the device 100, having first and second sections 104, 108 can more readily conform to an implant or expander shape, provide improved support to an implant or expander, or provide complete overlying tissue contact by virtue of spaces on the lateral sides of the joining section 110, i.e., between the second edges 111, 112, where a gap is formed.

FIG. 3 illustrates another breast treatment device 200 for more complete coverage of a breast implant or tissue expander, according to certain embodiments. As shown, the device 200 includes a sheet of acellular tissue matrix, wherein the sheet of acellular tissue matrix comprises a flexible sheet 200 with a top surface and a bottom surface (the surfaces correspond to the front and back of the two-dimensional image of FIG. 3).

The sheet 200 can be sized and shaped to allow coverage of a breast implant or tissue expander, provide improved support to an implant or expander, or provide complete overlying tissue contact. As shown, the sheet 200 has an upper curved border 210 having a first degree of curvature and a lower curved border 220 having a second degree of curvature. The upper border 210 and lower border 220 can be joined at lateral apices 224, 228, which can include a sharp angle or rounder edges.

As with the device 100 of FIG. 2, the device 200 can be sized and shaped to allow coverage of a breast implant or tissue expander, particularly for coverage of an anterior portion of the implant or expander when implanted in a prepectoral position. In addition or alternatively, the device can provide improved support to an implant or expander, or provide complete overlying tissue contact. In one embodiment, the lower curved border 220 is shaped and sized to conform to a desired shape of a lower margin of a breast, and the upper curved border 210 is sized and shape such that the flexible sheet of acellular tissue matrix can cover substantially all of the anterior surface of a breast implant to tissue expander Many implants or expanders will have a shape and size such that the implant volume at the lower pole is greater than that at the upper pole. The device 200 (as well as other devices described herein), allows coverage and support of such implants with little or no additional manipulation by surgeons (e.g., no cutting to size and shape). As such, the devices 200 (and 100, 300) prevent waste of valuable tissue matrix material, save substantial operating room time, and have preformed margins that produce a desired configuration when implanted.

The size and shape of the devices 100, 200, 300 can be selected based on typical implant or tissue expander (when fully expanded) shapes and volumes. For example, for the device 200 of FIG. 3, the device can include a lower section 230 and upper section 240 and the height or length of the lower and upper sections 230, 240 can be selected based on the desired implant or expander size and shape as well as a the need for additional material to cover tissue or affix the device to surrounding structures. Exemplary, sizes can include, for example a height (from the bottom or lower border 220 to top of upper border 210) from 15-25 cm, and a width from apices 224, 228 of 15-30 cm. For example, a small device may have a height of 15 cm and width of 17-18 cm; a medium device a height of 18-19 cm and width of 21-22 cm; and a large device a height of 20-21 cm and width of 23-24 cm; and an extra-large device a height of 22-23 cm and width of 26-27 cm.

FIG. 4 illustrates another breast treatment device 300 for more complete coverage of a breast implant or tissue expander. The device 300 can include a sheet 300 of acellular tissue matrix, wherein the sheet of acellular tissue matrix comprises a flexible sheet with a top surface and a bottom surface (the surfaces correspond to the front and back of the two-dimensional image of FIG. 4).

The sheet 300 can include a lower curved border 314 and an upper curved border 316, wherein the upper border 316 and lower border 314 are joined at apices 308, 309 at lateral ends of the device 300. As with the other devices 100, 200, the apices 308, 309 can be sharp angles or can be rounded.

The device 300 can have a configuration such that when lying on a flat surface, the sheet 300 is symmetrically shaped about an axis 320 midway between the apices 308, 309 and parallel to the top and bottom surfaces.

The device 300 can also be shaped such that the lower border 314 forms a single outward arc shape (lower section 302), and the upper border 316 has three arc sections 306, 306', 307, including first and second sections 306, 306' each extending from one of the apices 308, 309, and a third section 307 joining the first and second sections 306, 306', the third section having a degree of curvature that is different than the degree of curvature of the first and section 306, 306' sections. The arc sections 306, 306', 307 can form the upper portion or section 304, while the lower border 314 defines the lower section 302.

Figure 5A:
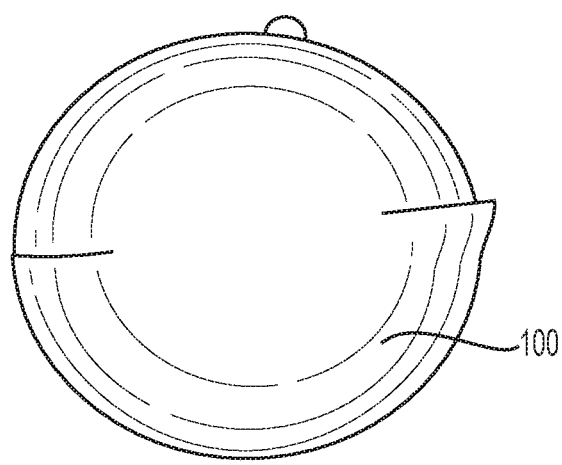
FIG. 5A is a frontal view of the breast treatment device including an acellular tissue matrix positioned over a breast implant to illustrate how the device provides coverage to the implant or tissue expander or supports the implant or reinforces surrounding tissue.

As discussed previously, the devices described herein can be used to allow coverage of a tissue expander or implant, including implants or expanders positioned in a prepectoral position. In addition or alternatively, the device can provide improved support to an implant or expander, or provide complete overlying tissue contact. As such, FIG. 5A illustrates a frontal view of the breast treatment device 100 including an acellular tissue matrix positioned over a breast implant to illustrate how the device provides coverage to the implant or tissue expander. It will be understood that when implanted, and as discussed further below, the tissue matrix will contact overlying dermal or subcutaneous tissue, as well as possible contact and connection with muscle or other tissues, and the matrix can support the implant, allow ingrowth of tissue, and provide tissue regeneration, support, and vascularization, in some cases for patients for whom insufficient tissue or insufficient tissue strength or vascularity would have been present in the absence of the tissue matrix. As such, the tissue matrix allows prepectoral positioning while avoiding other, often difficult procedures.

Figure 5B:
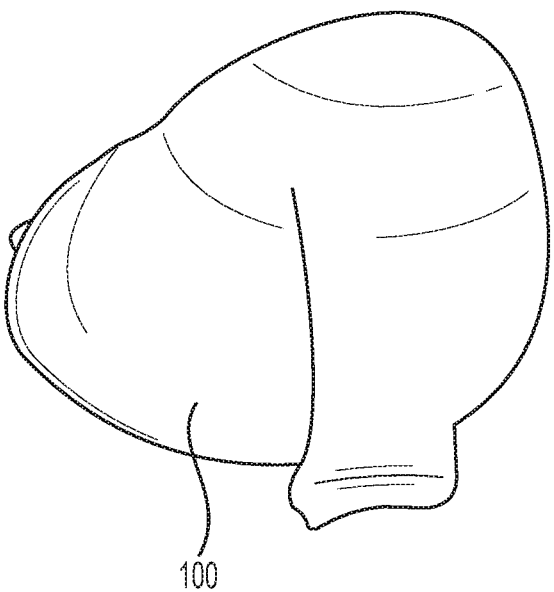
FIG. 5B is a side view of the breast treatment device of FIG. 5A including an acellular tissue matrix positioned over a breast implant to illustrate how the device provides coverage to the implant or tissue expander or supports the implant or reinforces surrounding tissue.
Figure 5C:
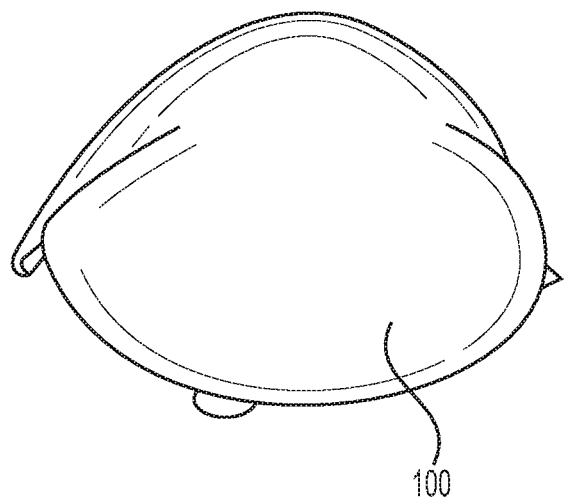
FIG. 5C is a top view of the breast treatment device of FIG. 5A including an acellular tissue matrix positioned over a breast implant to illustrate how the device provides coverage to the implant or tissue expander or supports the implant or reinforces surrounding tissue.
Figure 6A:
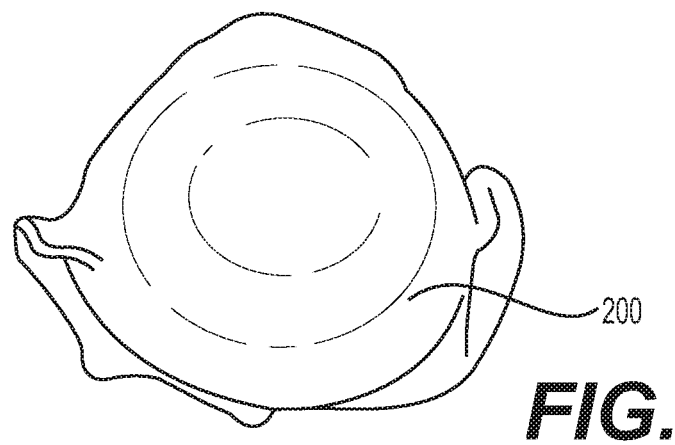
FIG. 6A is a frontal view of a breast treatment device including an acellular tissue matrix positioned over a breast implant to illustrate how the device provides coverage to the implant or tissue expander.
Figure 6B:
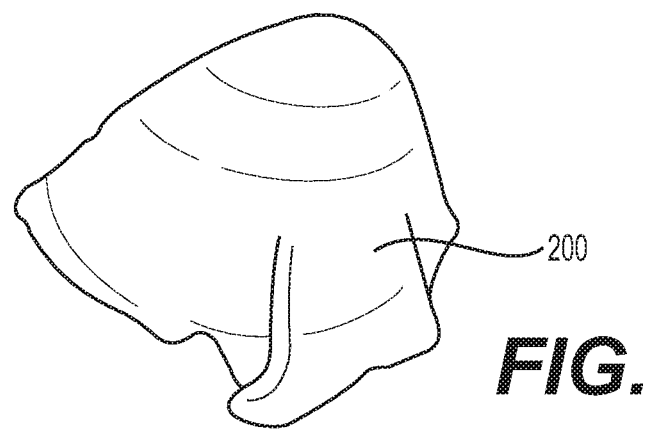
FIG. 6B is a side view of the breast treatment device of FIG. 6A including an acellular tissue matrix positioned over a breast implant to illustrate how the device provides coverage to the implant or tissue expander.
Figure 6C:
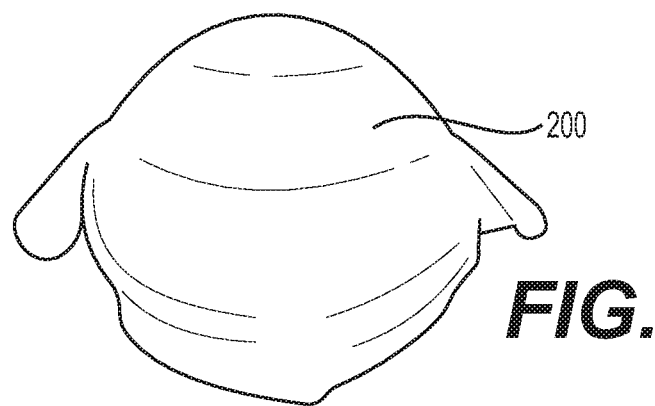
FIG. 6C is a top view of the breast treatment device of FIG. 6A including an acellular tissue matrix positioned over a breast implant to illustrate how the device provides coverage to the implant or tissue expander.
Figure 7A:
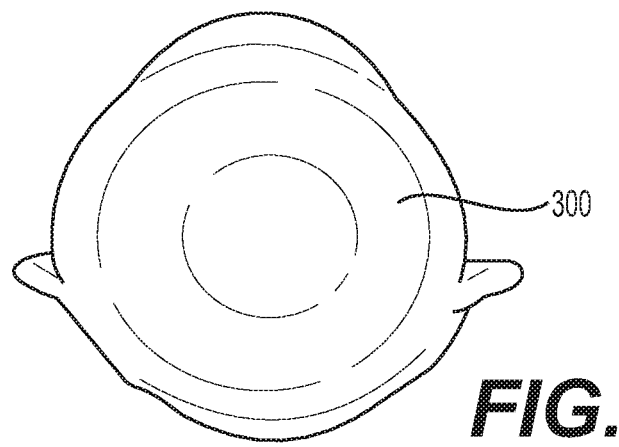
FIG. 7A is a frontal view of a breast treatment device including an acellular tissue matrix positioned over a breast implant to illustrate how the device provides coverage to the implant or tissue expander.
Figure 7B:
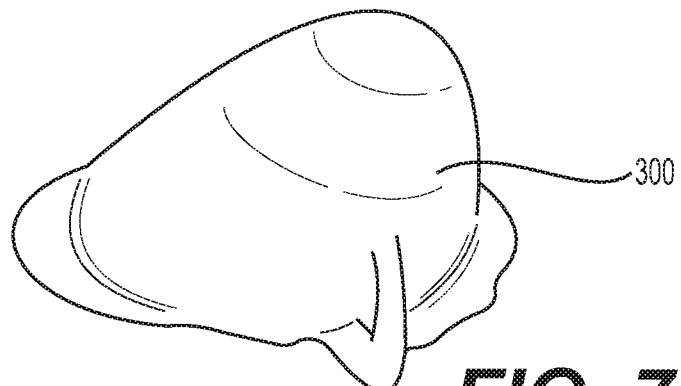
FIG. 7B is a side view of the breast treatment device of FIG. 7A including an acellular tissue matrix positioned over a breast implant to illustrate how the device provides coverage to the implant or tissue expander.
Figure 7C:
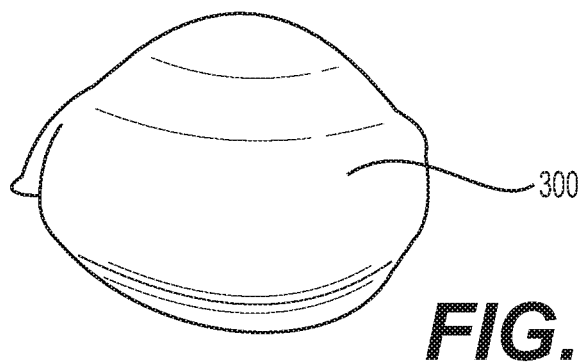
FIG. 7C is a top view of the breast treatment device of FIG. 7A including an acellular tissue matrix positioned over a breast implant to illustrate how the device provides coverage to the implant or tissue expander.

FIGS. 5B and 5C are side and top views, respectively, of the device of FIG. 5A. FIGS. 6A-6C provide comparable views of the device 200 of FIG. 3 over an implant; and FIG. 7A. FIGS. 7A-7C provide comparable views of the device 300 of FIG. 4 over an implant. It should be noted that the frontal view is described in reference to how the device and implant should be viewed with respect to a patient if the implant covered by the devices 100, 200, 300 were located on the anterior chest wall. So, for example, FIG. 5A is referred to as a frontal view as it is a view showing the front of the device 100 when covering an implant (behind the device) as it would be viewed from the front of a patient in whom the device is implanted.

Figure 8A:
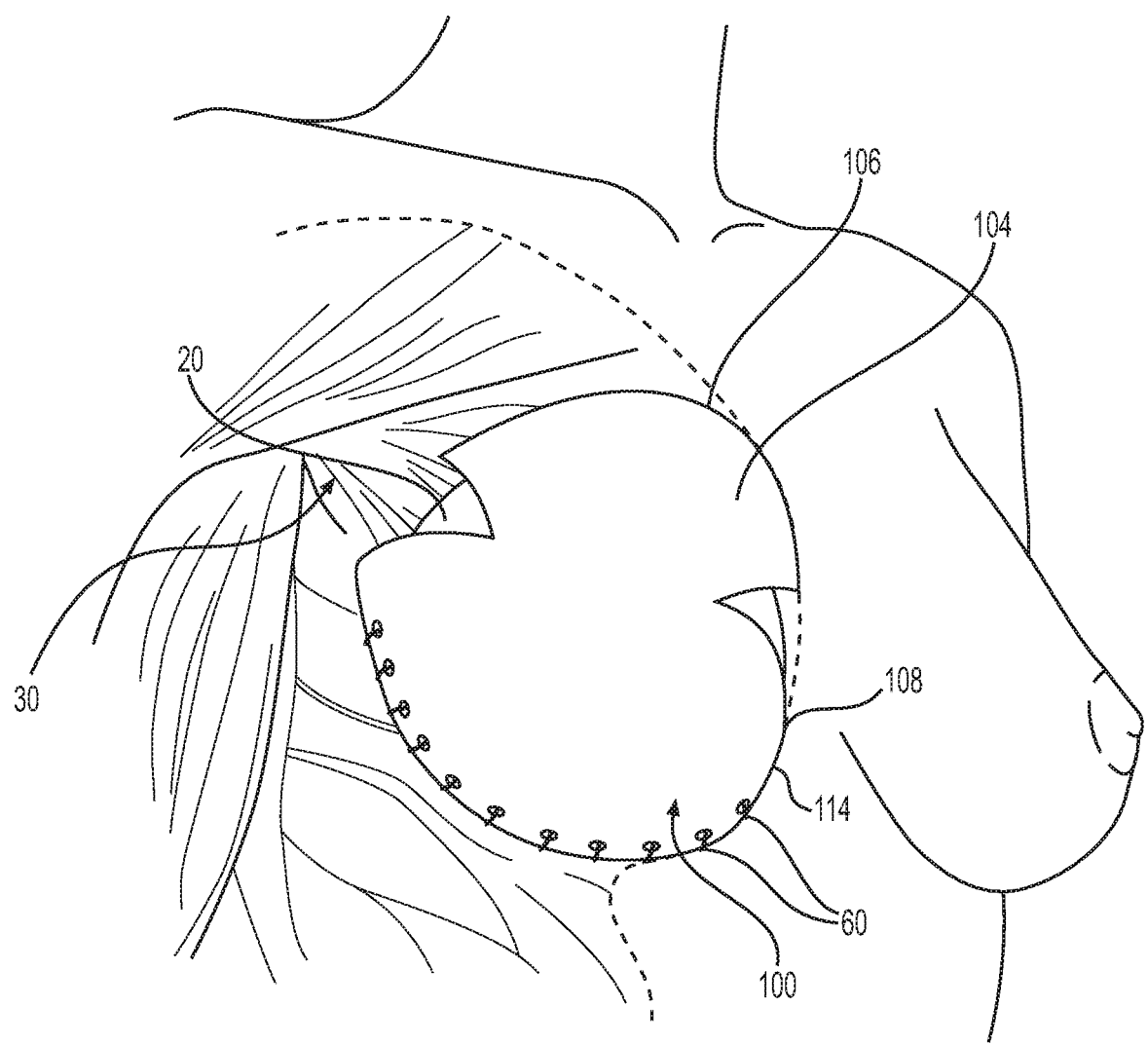
FIG. 8A illustrates implantation of the breast treatment device of FIG. 2 in a prepectoral position along with a breast implant.
Figure 8B:
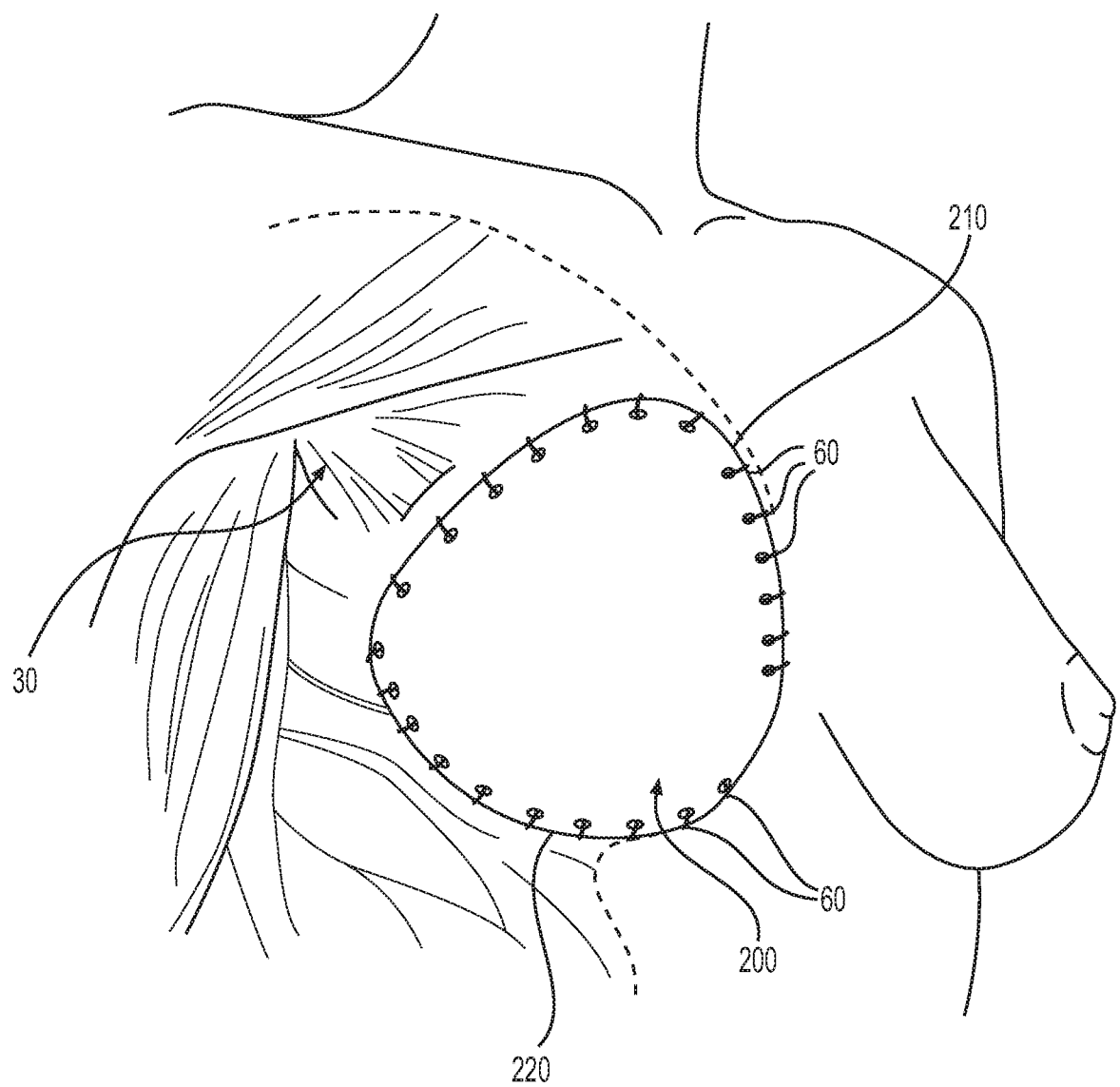
FIG. 8B illustrates implantation of the breast treatment device of FIG. 3 in a prepectoral position along with a breast implant.

FIG. 8A illustrates implantation of the breast treatment device 100 of FIG. 2 in a prepectoral position along with a breast implant. And FIG. 8B illustrates implantation of the breast treatment device 200 of FIG. 3 in a prepectoral position along with a breast implant. A similar implantation process and configuration would be applicable to the other devices 300 or variations thereof described throughout. As shown, the devices 100, 200 are implanted to cover an implant 20 or expander on an anterior portion of the chest wall 30. One section 108 (or upper and lower section of device 200) is positioned to cover a lower portion of the implant, while the other section 104 covers an upper portion of the implant 20.

To secure the devices 100, 200 (or any other device described herein) in place, parts of the device 100, 200, such as the lower border 114, 220 and/or upper border 106, 210 can be affixed to tissue using sutures, clips, staples, adhesives, or other suitable surgical fixation systems. In some cases, the device 100, 200 (or device 300) can be sized to provide an amount of tissue matrix that wraps around the posterior portion of the implant or expander, e.g., at the lower margin/inframammary fold and/or at the superior surface of the implant or expander. The devices may be sized to wrap between, for example, 1-3 cm, 1-2 cm around the posterior portion of the implant or expander at either or both of the inferior or superior portions of the implant or expander.

In some cases, the implant or tissue expander includes suture tabs or other fixation components to allow the device 100, 200, or 300 to be secured to the implant or expander. In such cases, the device can be joined to the expander or implant prior to or during implantation before final positioning within an implant site. In cases where the device 100, 200, 300 is sized to wrap partially around a posterior portion of the implant or expander, the tabs or fixation devices can be posteriorly located so that the device can be secured to the posterior aspect of the implant or expander, while the device is in contact with overlying subdermal tissues when implanted.

Figure 13:
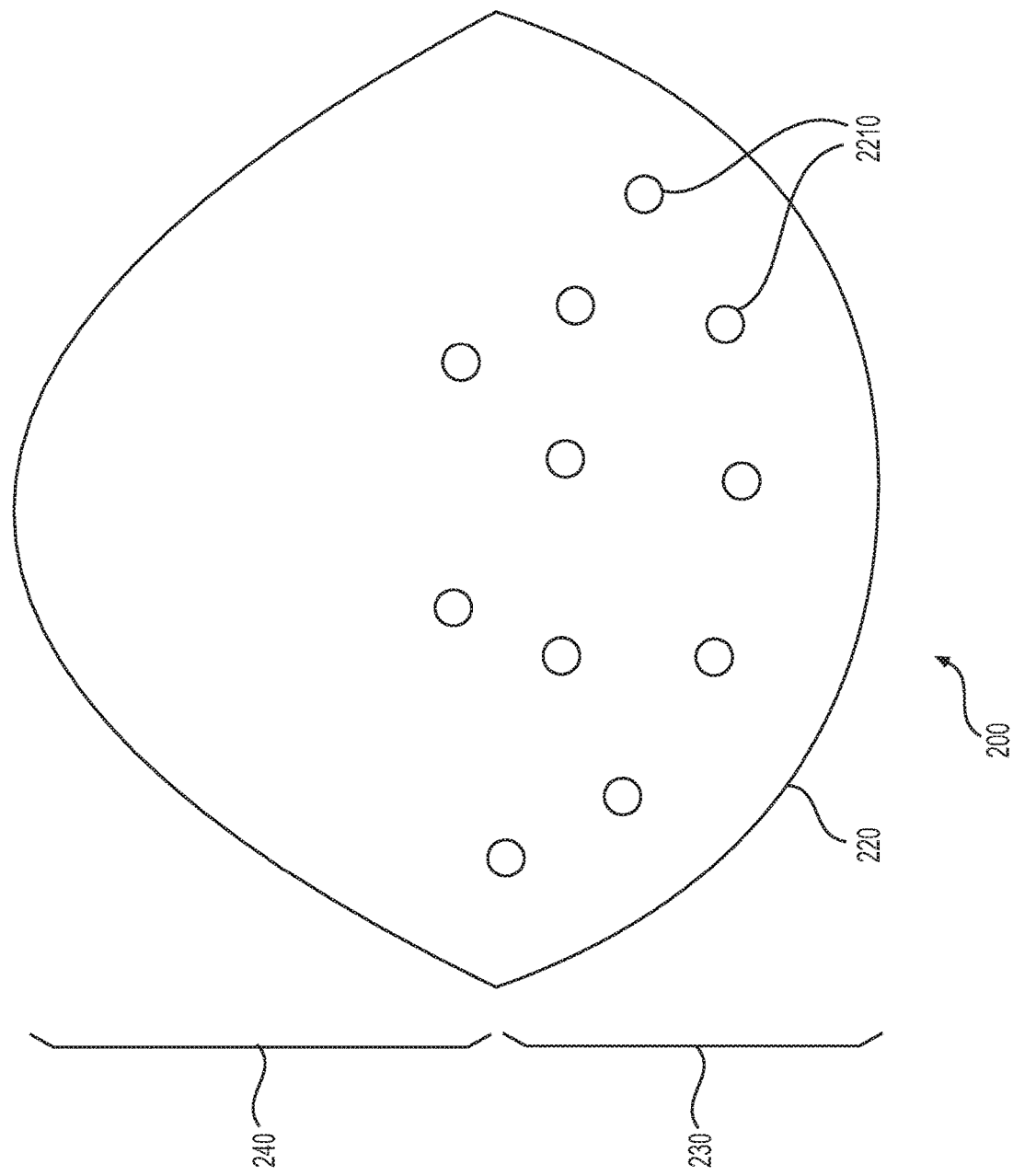
FIG. 13 illustrates a breast treatment device in accordance with the embodiments of FIG. 3 for more complete coverage of a breast implant or tissue expander and/or support or reinforcement of surrounding tissues, wherein the device further includes preformed holes or pilot holes, according to certain embodiments.
Figure 14:
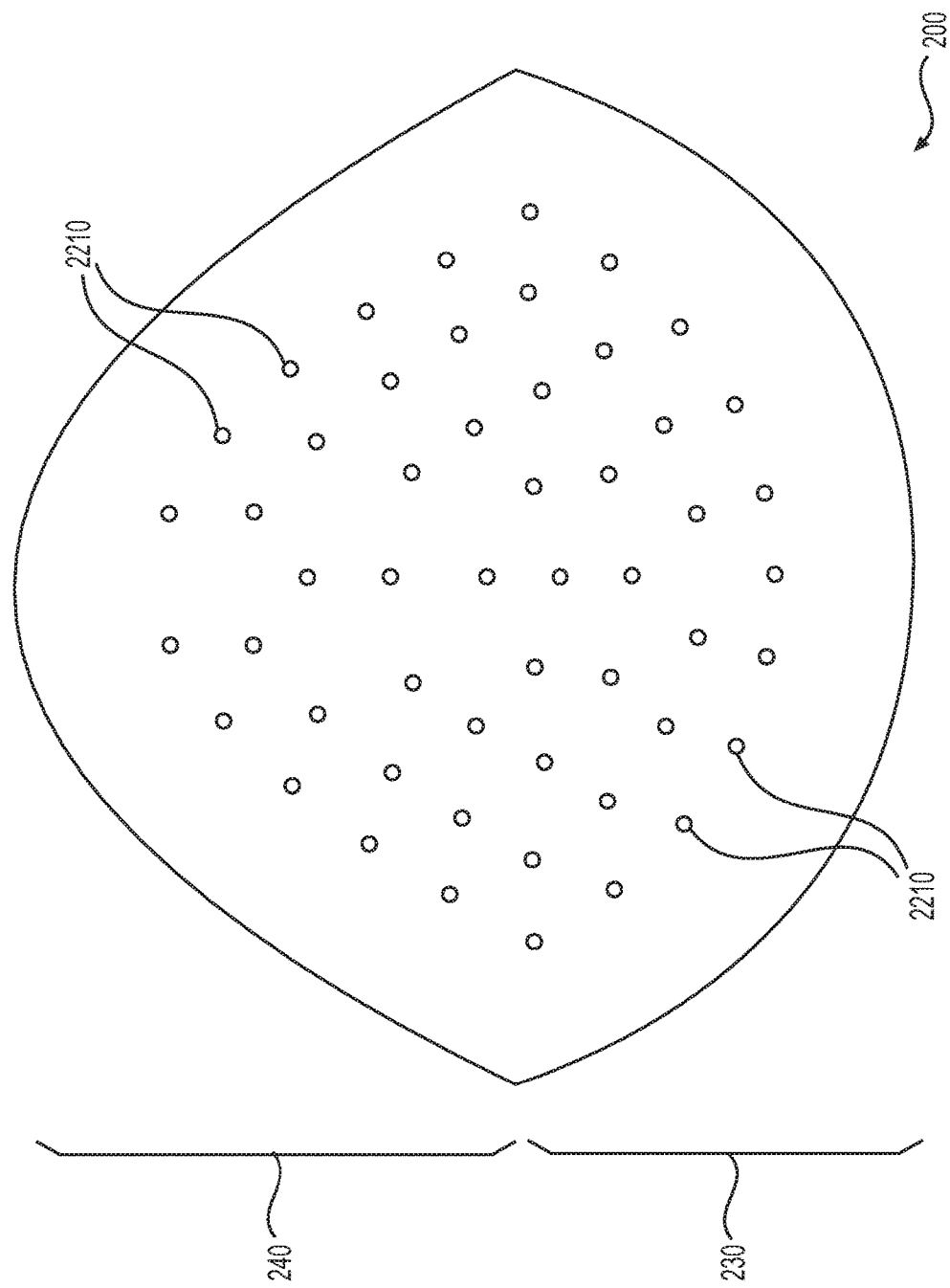
FIG. 14 illustrates another breast treatment device in accordance with the embodiments of FIG. 3 for more complete coverage of a breast implant or tissue expander and/or support or reinforcement of surrounding tissues, wherein the device further includes preformed holes or pilot holes, according to certain embodiments.

The devices described herein can further be modified to facilitate fixation to tissue for proper implantation. For example, the devices can include features that provide additional material for attachment to anchors such as sutures and/or can include features that guide proper or easier placement of sutures or other anchors. In addition, or alternatively, the devices can include openings, slits, or holes that provide for one or more of improved drainage or fluid flow, better coverage of the implant or expander, or changes in mechanical properties (e.g., more flexibility due to presence of slits, holes, or other mechanical modifications). FIGS. 9-14 illustrate various modified devices, and although shown with respect to the device shape of FIGS. 2 and 3 (FIGS. 13 and 14 illustrate embodiments of the device of FIG. 3, it will be understood that similar modifications can be used with the other described devices of FIG. 4.

FIG. 9 illustrates a breast treatment device 900, wherein the device further includes preformed tabs 910 or extensions for attachment to tissue, according to certain embodiments. The tabs or extensions 910 can provide additional area for passing sutures or other anchors, or can be specifically shaped to engage with fixations devices located on the surface of an implant or expander. Although a finite and specific number of tabs 910 is illustrated, additional or fewer tabs 910 may be used.

Figure 10:
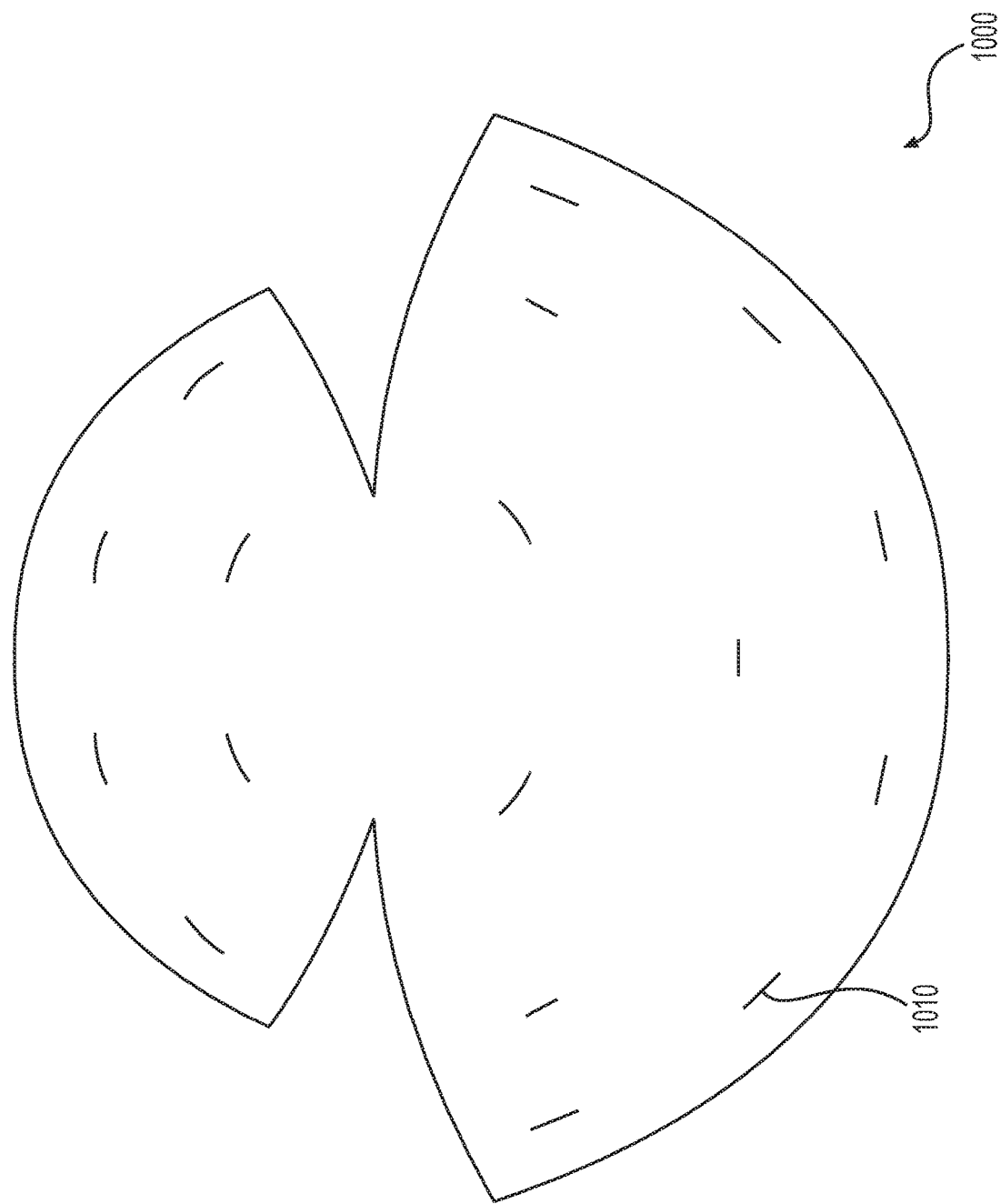
FIG. 10 illustrates a breast treatment device for more complete coverage of a breast implant or tissue expander and/or support or reinforcement of surrounding tissues, wherein the device further includes preformed slits or openings, according to certain embodiments.

FIG. 10 illustrates a breast treatment device 1000, wherein the device further includes preformed slits 1010 or openings, according to certain embodiments. The slits 1010 or openings can allow flow of fluid through the tissue matrix, thereby preventing certain complications (e.g., seroma or inability to drain infectious fluids). In addition, the slits 1010 can be shaped and sized to allow expansion or more flexible coverage of an implant or expander.

Figure 11:
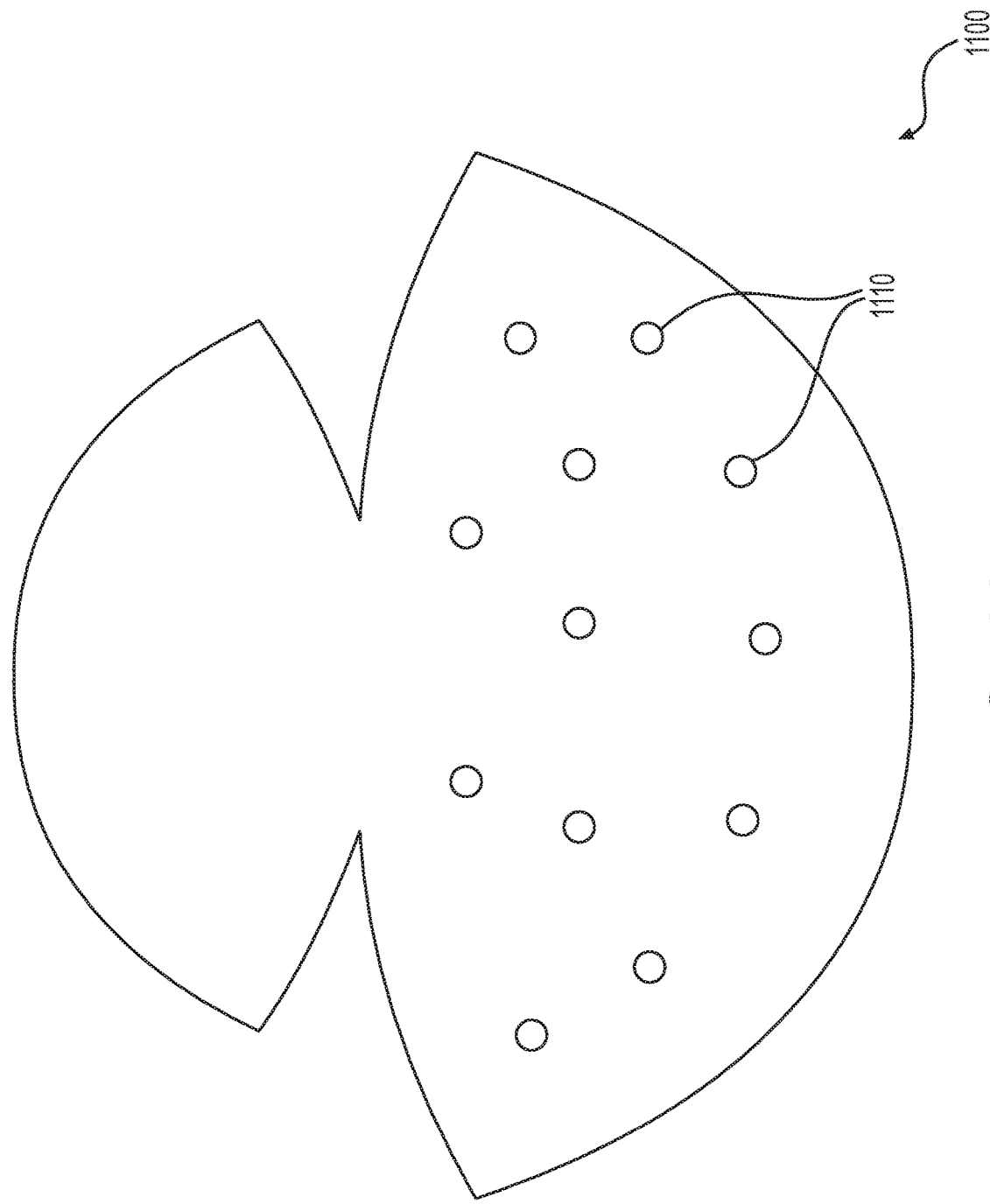
FIG. 11 illustrates a breast treatment device for more complete coverage of a breast implant or tissue expander and/or support or reinforcement of surrounding tissues, wherein the device further includes preformed holes or openings, according to certain embodiments.

FIG. 11 illustrates a breast treatment device 1100, wherein the device further includes preformed holes 1110 or openings, according to certain embodiments. Similar to the openings 1010 of FIG. 10, the holes 1110 can allow fluid to flow through the material. The openings 1110 and slits 1010 can be arranged in number, size, and location based on a variety of factors.

Figure 12:
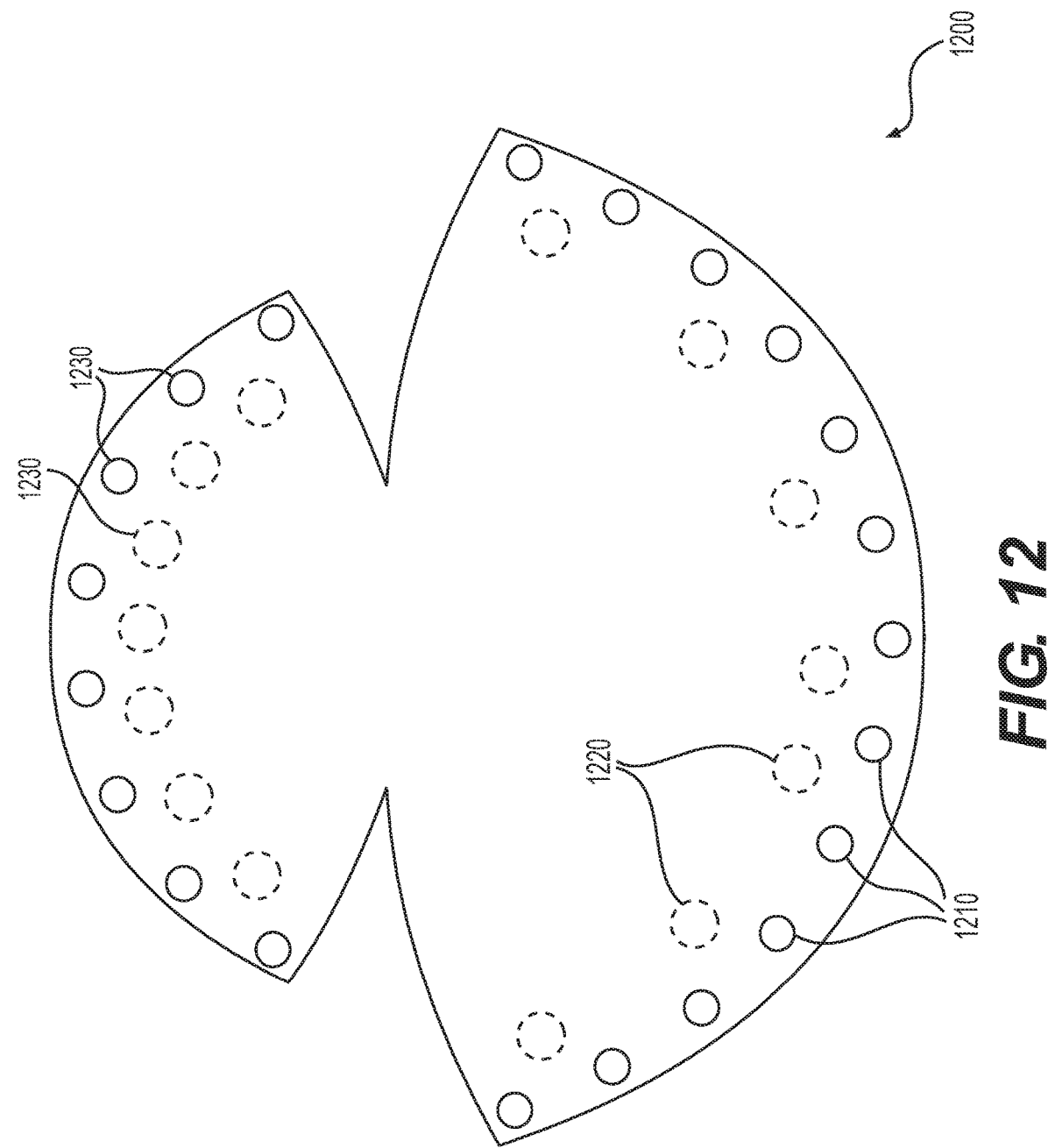
FIG. 12 illustrates a breast treatment device for more complete coverage of a breast implant or tissue expander and/or support or reinforcement of surrounding tissues, wherein the device further includes preformed holes or pilot holes, according to certain embodiments.

FIG. 12 illustrates a breast treatment device 1200, wherein the device further includes preformed holes or pilot holes (holes and pilot holes represented by any of 1210, 1220, or 1230), according to certain embodiments. The holes or pilot holes 1210 can be provided to allow easier, more rapid, or better fixation. For example, the holes or pilot holes can be positioned in a row or locations that correspond to a desired spacing or positioning to provide secure fixation, e.g., along the lower border corresponding to the inframammary fold when implanted. The holes or pilot holes can pass completely through the device to allow passage of sutures or other anchors, or can include a countersink or divot formation to provide an area of less density or strength to allow easy anchor passage.

The holes or pilot holes can be positioned on the lower section of the device (holes 1210, 1220) and/or upper section 1230 near edges. In addition, holes or pilot holes may be formed at other regions if desired. Further, the holes or pilot holes can be in two or more rows, as illustrated, to allow multiple points of fixation and/or to give the surgeon some choice in selecting holes location.

Similar to FIG. 12, FIGS. 13 and 14 illustrate embodiments of the device 200 of FIG. 3, but further including holes, openings, or pilot holes. As shown in FIG. 13, the holes, openings, or pilot holes 2210 may be localizes to a portion of the device, e.g., the lower section, thereby providing openings only around the lower pole of the implant or tissue expander. Alternatively, the holes, openings or pilot holes can be arranged in other patterns or throughout the surface of the device, as shown in FIG. 14.

The holes, openings, and pilot holes will generally be positioned and of a number such that they do not cause an undesirable loss of strength or area for cellular ingrowth. In addition, the holes, openings, or pilot holes may be a distance from the edges of the devices such that they do not overlap with areas where sutures may be placed, or alternatively, can be placed to provide preformed opening/pilot openings to guide where sutures may be placed.

In some cases, the tissue matrices can be produced from materials that include a basement membrane on at least one surface. For example, the devices can be produced from an acellular dermal matrix, and either the top surface or bottom surface can include an epithelial basement membrane across the surface. When implanted next to a breast implant or tissue expander, the basement membrane covered surface may face towards the implant or tissue expander such that the surface not including a basement membrane faces overlying vascularized tissue.

Methods of treatment using the devices discussed herein as well as devices produced for use in such methods are further contemplated as within the scope of the present inventions. The methods are illustrated and discussed above with respect to FIGS. 8A and 8B, and aspects of the methods are elaborated upon herein. The devices can be used for improving various procedures, such as prepectoral implantation of an implant. In many cases, the method will first include performing a procedure to remove tissue, e.g., for surgical oncology, and can therefore, include mastectomy, lumpectomy, or variations on those procedures. The methods and device may also be used for augmentation procedures without, or in a separate procedure from mastectomy or other procedures (e.g., for staged reconstruction). When used for implantation for augmentation, or in a subsequent procedure, a surgeon may first form a pocket or space in the subcutaneous region.

After performing a mastectomy or other procedure and ensuring a proper space for the implant or expander, a surgeon may then place the tissue matrix materials described herein within the space, and affix portions of the tissue matrices to tissues such as the chest wall or muscle, as illustrated in FIGS. 8A and 8B. As an example, the tissue can be affixed to the superior medial and lateral edges of the pectoralis major and to fascial at the level of the inframammary fold. As such, the tissue matrix comes in contact with overlying tissue (e.g., dermis) and is prepared to provide support to the implant or expander and subsequently allow tissue ingrowth and vascularization of overlying tissue.

Next, and implant or expander can be placed within the pocket, and remaining edges of the tissue matrix are sutured or otherwise attached to tissue to close the implant pocket, followed by closure of the surgical site.

It will be appreciated that the tissue matrix may alternatively be wrapped around the implant or expander outside the body, and the entire device (e.g., implant/expander and tissue matrix) can then be placed in the surgical site. Further, implants or expanders may include a structure for securing to the tissue matrix and/or chest wall or other tissue.

Other embodiments will be apparent to those skilled in the art from consideration of the specification and practice of this disclosure. It is intended that the specification and examples be considered as exemplary only, with the true scope and spirit of the disclosed devices and methods being indicated by the following claims.

What is claimed is:
1. A breast treatment device, comprising:
a sheet of acellular tissue matrix, wherein the sheet of acellular tissue matrix comprises a flexible sheet with a top surface and a bottom surface, wherein the sheet has a continuous upper curved border having a first degree of curvature and a continuous lower curved border having a second degree of curvature, wherein the continuous upper curved border and continuous lower curved border are joined at lateral apices separated by a distance between about 15-30 cm and the continuous upper curved border and continuous lower curved border define a height of at least 15 cm to allow complete coverage of an anterior surface of a breast implant, wherein the continuous lower curved border is shaped and sized to conform to a desired shape of a lower margin of a breast;

an upper section extending between the upper curved border and the lateral apices; and a lower section extending between the lower curved border and the lateral apices;

wherein the upper section has a larger surface area and a larger height than the lower section.

2. The device of claim 1, wherein the sheet of acellular tissue matrix comprises a dermal tissue matrix.

3. The device of claim 1, wherein the acellular tissue matrix is a porcine tissue matrix.

4. The device of claim 1, wherein the acellular tissue matrix is a human tissue matrix.

5. The device of claim 1, wherein the device further comprises a breast implant or tissue expander.

6. The device of claim 1, wherein the acellular tissue matrix include one or more holes or openings.

7. The device of claim 6, wherein the holes or openings include a group of holes passing through the tissue matrix.

\* \* \* \* \*